United States Patent [19]

Chang et al.

[11] 3,932,243

[45] Jan. 13, 1976

[54] CLEANING AND POLISHING COMPOUND FOR BARREL AND VIBRATORY FINISHING OF FERROUS AND NON-FERROUS METALS

[75] Inventors: Edward H. Chang; Oliver D. Nichols, both of Burnsville, Minn.

[73] Assignee: Fremont Industries, Inc., Shakopee, Minn.

[22] Filed: Dec. 18, 1974

[21] Appl. No.: 533,938

Related U.S. Application Data

[63] Continuation-in-part of Ser. No. 381,359, July 20, 1973, abandoned.

[52] U.S. Cl. .................... 156/20; 134/3; 134/23; 252/79.4
[51] Int. Cl.² ........................................ C23G 1/36
[58] Field of Search ......... 134/3, 23, 32, 33, 38–41; 156/2, 18, 20; 252/79.1, 79.2, 79.4; 260/980, 951, 978

[56] References Cited

UNITED STATES PATENTS

| | | | |
|---|---|---|---|
| 2,087,230 | 7/1937 | Bigeon | 156/19 X |
| 3,072,515 | 1/1963 | Von Smolinski | 156/20 |
| 3,776,985 | 12/1973 | Nehmsmann | 260/980 |

*Primary Examiner*—William A. Powell
*Attorney, Agent, or Firm*—Orrin M. Haugen

[57] ABSTRACT

A formulation for the surface treatment of metal articles wherein the article to be treated is immersed and agitated in a working solution of the formulation. The formulation consists essentially of the esterification reaction product of phosphoric acid based upon $P_2O_5$ with an alkylphenol of either octylphenoxypoly (ethyleneoxy) ethanol or nonylphenoxypoly (ethyleneoxy) ethanol, and wherein the mol ratio of the reactants ranges from between about 1:3 up to about 3:4 of $P_2O_5$ to alkylphenol.

7 Claims, No Drawings

CLEANING AND POLISHING COMPOUND FOR BARREL AND VIBRATORY FINISHING OF FERROUS AND NON-FERROUS METALS

CROSS-REFERENCE TO RELATED APPLICATION

The present invention is a continuation-in-part of our copending application Ser. No. 381,359 filed July 20, 1973, and entitled "Cleaning and Polishing Compound for Barrel and Vibratory Finishing of Ferrous and Non-Ferrous Metals", now abandoned, and is related to our copending application Ser. No. 375,172, filed June 29, 1973, entitled "Polishing Compound for Barrel and Vibratory Finishing of Ferrous and Non-Ferrous Metals."

BACKGROUND OF THE INVENTION

The present invention relates generally to the preparation of an improved partial phosphate ester formulation for the surface treating of metallic articles, including both ferrous and non-ferrous articles, wherein a single formulation may be employed for the concurrent operations of cleaning, de-greasing, de-scaling, and polishing of the article. Agitation of the metal articles is obtained in a conventional barrel or vibratory finishing machine wherein the articles are immersed and agitated through either tumbling or vibration, and may, in certain instances, be immersed in a media such as an abrasive media.

At the present time, various formulations of chemical compositions have been utilized for the purpose of conducting single operations on metal articles in order to achieve a desired surface finish. For example, those compositions most frequently employed include sodium or potassium hydroxide, phosphates, carbonates, silicates, clays, soaps, and the like. While each of these materials may perform certain of the operations in a functional fashion, such as, for example, either cleaning, de-greasing, de-scaling or polishing, the materials nevertheless required the use of multiple step treatment.

The quality of the finish obtained on the metal surface has been primarily influenced by the performance of the various soaps, primarily those soaps derived from animal tallow, coconut oil, or other triglycerides, with these materials having been utilized primarily in barrel or vibratory metal finishing machines.

As indicated, a plurality of individual steps has normally been required in order to obtain acceptable metal surface finishes. Soaps and soap-containing products frequently produce undesirable side effects due to their behavior in hard water, including the formation of soap scum with calcium bicarbonates, poor water rinsibility, slow polishing action, as well as a partial congealing of the cleaning medium. On some occasions, the free alkalinity present in the soap products due to the manufacturing techniques employed presented some difficulties in treating of certain surface finishes, such as aluminum.

As a result of these difficulties, many synthetic or natural metal finishing media have been utilized in order to accomplish a shortening of the processing time, as well as processing steps and operations required. These various materials which have been employed have been found, however, to be inadequate either for accomplishing the entire surface treatment operation in a single batch operation, or in accomplishing the task in a reasonable period of time.

Typically, a barrel finishing machine is an apparatus with either an open or closed hexagonal or similarly shaped enclosure. These finishing machines are available in varying sizes, depending upon the application, and are arranged to rotate in one operational direction at a controllably variable speed. The rotational speed is normally selected as a function of the compartment size, the volume of parts and weight present in the charge, as well as the media ratio being employed. Other parameters include the type of material utilized in the surface treatment material, the water volume present, as well as the processing time normally available.

Vibratory finishing machines, which are also conventionally employed, normally utilize an open housing or the like equipped with a variable speed drive arranged to oscillate the housing at a certain frequency, ranging for example, from several hundred of cycles up to several thousands of cycles per minute. The parameters present which determine the proper drive frequency include the compartment size, the type of parts as well as weight of parts present, the media ratio such as an abrasive media when employed, the type of material employed as the surface treatment composition, as well as the processing time available. Both barrel finishing machines and vibratory finishing machines are commercially available.

As has been indicated, several individual operations or steps are normally employed in order to achieve the desired surface finish. These steps are identified briefly as follows:

Step 1 — Clean the product, including de-greasing, deburring and de-scaling (cleaning media optionally present).
Step 2 — Rinse.
Step 3 — Utilize neutralizer rinse in case de-scaling formulation employed.
Step 4 — Rinse.
Step 5 — Burnish or polish, media being optionally present.
Step 6 — Rinse.

The above listing indicates the minimum steps required to obtain a polished effect on the surface of a metal part. The time required for each of these individual operations may vary from several minutes up to several hours, depending upon the condition of the non-treated product, the surface finish desired, and the nature of the finished product. In other words, the characteristics of the part being treated will normally determine the processing time.

SUMMARY OF THE INVENTION

In accordance with the present invention, a synthetic cleaning and polishing formulation is provided with soaplike physical properties, with the characteristics providing no adverse effects during use. In other words, the cleaning component is utilized as a substitute for those natural soaps which may be employed for mild applications but which is aggressive in its action on steel surfaces. The formulation further provides a finished product having a surface which is both stable to ordinary ambients, and is polished. The formulation makes it possible to achieve all of those steps indicated hereinabove, that is, Steps 1 through 5, in a single batch operation, and in some instances, those operations in Steps 1 through 6.

Briefly, in accordance with the present invention, at least a partial esterification of an alkylphenol with $P_2O_5$ is carried out wherein the alkylphenol is selected from the group consisting of octylphenol with the structural formula:

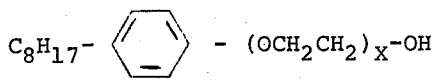

wherein X is an integer having an average volume of between 1 and 30; and nonylphenol having the structural formula:

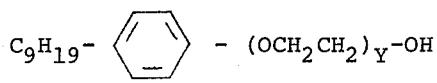

wherein Y represents an integer having an average value of between 5 and 13. The alkylphenols are reacted with $P_2O_5$ in the form of anhydrous $P_2O_5$, 105% polyphosphoric acid, or 115% polyphosphoric acid. The molar ratio of the reactants is preferably between 1:3 and up to 3:4 of $P_2O_5$/alkylphenol. The reaction conditions are normally carried forward for a period of from 3 to 5 hours at temperatures of from between 190° – 210°F.

Therefore, it is a primary object of the present invention to provide an improved formulation for use in an aqueous solution for surface treatment of metal articles, the working solution making it possible to clean, de-grease, deburr, de-scale, burnish and polish the article in a single processing operation.

It is a further object of the present invention to provide an improved formulation for the preparation of working solutions to clean and polish metal surfaces, with the formulation consisting essentially of the reaction product of alkylphenols such as octylphenoxylpoly (ethyleneoxy) ethanol and nonylphenoxypoly (ethyleneoxy) ethanol with various forms of phosphoric acid, and based upon $P_2O_5$.

It is yet a further object of the present invention to provide an improved formulation which is particularly adapted for the preparation of working solutions to be employed in barrel finishing machines and vibratory finishing machines for the treatment of surfaces of metal articles.

It is yet a further object of the present invention to provide an improved formulation, particularly adapted for the treatment of the surfaces of metal articles, wherein the formulation is based essentially upon the reaction product obtained from an alkylphenol selected from the group consisting of octylphenoxypoly (ethyleneoxy) ethanol and nonylphenoxypoly (ethyleneoxy) ethanol.

Other and further objects of the present invention will become apparent to those skilled in the art upon a study of the following specification and appended claims.

DESCRIPTION OF THE PREFERRED EMBODIMENT

In order to present the various formulations which find utility in accordance with the present invention, the following examples are provided:

EXAMPLE 1

A total of 1 mol of octylphenoxypoly (ethyleneoxy) ethanol having the structural formula:

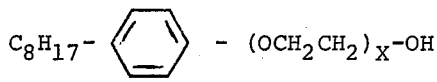

having the value of X selected to provide an average molecular weight of about 646 was utilized. Such material is commercially available from GAF Corporation, Chemical Division, of New York, New York, under the code name "Igepal CA-630". This alkylphenol was reacted with 0.75 mol of $P_2O_5$ of 115% $H_3PO_4$ for a period of 4 hours at a temperature maintained between 190° – 210° F. A working solution containing 1% by weight of the reaction product in water was utilized to polish aluminum metal grommets of the type employed for athletic shoes. Good polishing performance was obtained in a period of approximately 1 hour. As a control, a total of 6 hours of exposure to soap solutions was required to obtain an equally cleaned surface.

EXAMPLE 2

The reactants employed in Example 1 were selected with a total of 0.5 mol of $P_2O_5$. These reactants were reacted for a period of 5 hours at temperatures ranging between 190° – 210° F. The analysis of the reaction product indicated some phosphoric acid being present. The product is useful in a 1% by weight working solution for polishing the surface of metal articles including ferrous and non-ferrous materials.

EXAMPLE 3

The individual reactants utilized in Example 1 were again employed with the $P_2O_5$ being increased to 1.0 mol. This material is reacted for a period of 3 hours at temperatures from 190° – 210° F. This formulation is particularly adapted in a working solution at 1% by weight in water.

EXAMPLE 4

A total of 1 mol of octylphenoxypoly (ethyleneoxy) ethanol having the structural formula:

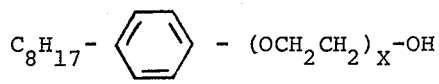

having the value of X selected to provide an average molecular weight of about 646 was utilized. This alkylphenol was reacted with 0.75 mol. of anhydrous $P_2O_5$ for a period of 4 hours at a temperature maintained between 190°–210° F. The reaction product was aimilar to that obtained in Example 1 hereinabove.

EXAMPLE 5

The individual reactants utilized in Example 1 were employed, with the exception being that 105% polyphosphoric acid was employed. A finished product having the same essential characteristics as was obtained with the reactants of Example 1 was obtained.

EXAMPLE 6

A total of 1 mol of an alkylphenol having the structural formula as set forth in Example 1, but having the value of X selected to provide a product with an average molecular weight of about 1086 was selected. This material was reacted with 0.75 mol of $P_2O_5$ of 115% $H_3PO_4$ for 4 hours at temperatures maintained between 190° – 210° F. This material is used in a 1% aqueous solution to provide a working solution with exceptional polishing performance on brass grommets. The polishing performance obtainable in 1 hour compared favorably with that obtainable with conventional soap when undertaken for a period of 4 hours.

EXAMPLE 7

The reactants as set forth in Example 6 were employed to prepare a reactant mixture, with only 0.5 mol of $P_2O_5$ being employed. This material was reacted for a period of 5 hours at temperature held between 190° – 210° F., with the analysis of the reaction product indicating a substantially lower quantity of the free alkylphenol being present. This material is useful in a 1% working solution in water.

EXAMPLE 8

The reactants as set forth in Example 6 were employed to prepare a reactant mixture, with 1.0 mol of $P_2O_5$ being employed. These reactants were reacted for a period of 4 hours at temperatures held between 190° – 210° F. This reaction product may be employed in working solutions in concentrations as low as 0.25 percent, with 1 percent and greater concentrations normally being preferred.

EXAMPLE 9

A total of 1 mol of a nonylphenol having the structural formula:

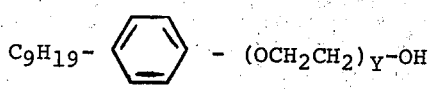

wherein Y has a value of approximately 9 was selected. Such materials are commercially available. This material was reacted for a period of 4 hours with a total of 0.75 mol of $P_2O_5$ of 115% $H_3PO_4$. The reaction product is useful in a 1% working solution in water, and was found to provide a surface finish after exposure to steel punched parts equivalent to that obtainable with exposure to soap under similar treatment for a period of 3 hours. Since the alkylphenol portion has relatively low water solubility, it has been found to be quite aggressive in its initial response or action toward steel surfaces.

EXAMPLE 10

The reactants as set forth in Example 9 were employed, however, in this case with only 0.5 mol of $P_2O_5$ being present. The reactants were reacted for a period of 5 hours at temperatures ranging from 190° – 210° F., with the reaction product having an analysis with modestly lower quantities of ester and phosphoric acid being present, along with some free alkylphenol. The formulation is desirable for use in connection with surface treatment of steel products, particularly those having grease and scale present on the surfaces.

EXAMPLE 11

The reactants as set forth in Example 9 were again employed, with the $P_2O_5$ content being increased to 1.0 mol. These reactants were placed in a vessel and reacted for a period of 4 hours at temperatures ranging between 190° – 210° F., with the resultant product having an analysis similar to that obtained in Example 9, but with a greater portion of phosphoric acid being present.

EXAMPLE 12

A total of 1 mol of a nonylphenol having the structural formula:

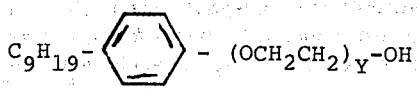

was utilized wherein the value of Y was about 13, with such material being known as Nonoxynol 13, and was mixed with a total of 0.75 mol of $P_2O_5$ of 105% $H_3PO_4$. These materials were reacted for a period of 4 hours at 190° – 210° F. and provided a reaction product useful in a 1% working solution in water. Excellent results may be achieved with steel punched parts.

EXAMPLE 13

When the individual parts to be treated are too large to be accommodated by self-tumbling or vibratory finishing, then a natural or synthetic solid inert media may be incorporated to cushion the parts during treatment. This is particularly true when parts are primarily non-symmetrical in their configuration. By way of natural or synthetic media, the following may be employed:
Pre-formed ceramic;
Plastic shapes;
wood or pine abrasives;
Random shaped fused aluminum oxide chips, or particles;
Abrasive powders or granules such as silica, pumice, aluminum oxide and others.

As is conventional in the art, an average ratio of approximately 3:1 media to workpiece is employed. For most metal parts, natural or synthetic media may be employed when the parts are heavily non-symmetrical or weigh more than approximately one-half pound each.

In this operation, the individual parts are placed within a tumbler with a ratio of 3:1 silica powder to workpiece, by weight. Thereafter, the silica is wetted with the formulation of Example 1, with the solution content being sufficiently low so as to permit continuous flow of the work and media. The treatment is otherwise, of course, the same as set forth in Example 1.

GENERAL DISCUSSION

The formulations as set forth in the above examples find utility in the treatment of metal articles prepared from iron, steel, stainless steel, aluminum, as well as with cooper and its zinc and tin containing alloys such as brass and bronze. The cleaning, rinsing, de-scaling, and other steps necessary prior to burnishing or polishing are accomplished in a single operation. When soaps are being employed for the polishing operation, a separate cleaning step is normally required in advance in order to prevent the redeposition of soils on the surface prior to the completion of the polishing operation.

Those products prepared in accordance with the procedures set forth in Examples 1–13, these multiple steps are eliminated and the processing time and steps are effectively shortened. It appears that the phosphate ester compounds are effective replacement products for animal or vegetable soaps which are in common use today. These selectively reacted phosphate ester compounds form a modest quantity of surface bubbles, comparable to those formed in connection with animal soap or vegetable soap products. Furthermore, these phosphate esters in acidic forms are effective petroleum oil emulsifiers, and hence are particularly adapted for use in connection with metallic parts prepared by conventional metal working techniques.

Chemically, the phosphate ester compounds prepared in accordance with the present invention contain reacted as well as unreacted acids, with these acids being present at certain concentrations in water which are sufficient to provide a micro-etch on the surface of the metallic articles being treated. This micro-etch occurs on both ferrous and non-ferrous metals and metal products. Upon being subjected to the micro-etch operations, the treated parts are more susceptible to the polishing operation which is, of course, occurring concurrently therewith. Since the phosphate esters prepared are strong oil emulsifiers, soils, once removed, do not redeposit on the surface of the articles during the polishing operation.

In Examples 1–13 hereinabove, the phosphoric acid constituent was indicated as being provided as the polyphosphoric acid. Obviously, the phosphoric acid, based upon $P_2O_5$, may be provided in meta-phosphoric acid, orthophosphoric acid, as well as pyro-phosphoric acid, and anhydrous $P_2O_5$. In other words, phosphoric acids are formed from the same oxide, $P_2O_5$, by different degrees of hydration. In the present situation, as the degree of hydration increases, the reaction time as well as the reaction temperature should be modestly increased, with the same reaction product being formed.

The working solutions preferably contain from between about ¼ percent up to about 10 percent of the reaction product. It has been found that if less than about ¼ percent of the product is employed in the working solution, the times involved for completing the process become unusually long, as the formulation is essentially too dilute. When concentrations greater than about 10 percent of the reactant product in the working solution are employed, the surface of the metal article may become darkened due to the presence of substantial quantities of free acid. While the free acid is partially consumed in the operation, the presence is, nevertheless, a potential problem when greater than about 10 percent of the reaction product is employed.

These partial phosphate esters of alkylphenols selected from the group consisting of octylphenoxypoly(ethyleneoxy) ethanol and nonylphenoxypoly(ethyleneoxyl) ethanol have an exceptionally long shelf or tray life and are substantially resistant to extensive hydrolysis, under normal conditions.

We claim:

1. The method of polishing the surface of a metal article which includes immersing and agitating the article in an aqueous solution comprising:

a. the reaction product obtained from the reactant mixture of an alkylphenol selected from the group consisting of an octylphenol having the structural formula:

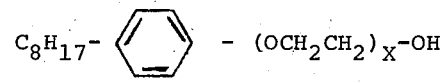

wherein X represents an integer having an average value of from between about 1 and 30; and a nonylphenol having the structural formula:

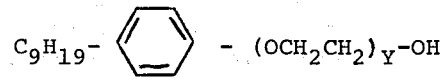

wherein Y represents an integer having an average value of from between about 5 and 13; and phosphoric acid based upon $P_2O_5$ in a molar ratio of between 1:3 and up to 3:4 of $P_2O_5$ to alkylphenol.

2. The method as set forth in claim 1 being particularly characterized in that said reaction product is contained in a working solution in the range of from between about ¼ percent to about 10 percent.

3. The method as set forth in claim 1 being particularly characterized in that said molar ratio is substantially 3:4.

4. The method as set forth in claim 1 being particularly characterized in that said reactants are reacted at a temperature of between about 190° – 210° F. for a period of between about 3 – 5 hours.

5. The method as set forth in claim 1 being particularly characterized in that said method is employed in the polishing of the surfaces of metal selected from the group consisting of iron, steel, stainless steel, aluminum, copper and its zinc and tin alloys.

6. The method as set forth in claim 1 wherein said phosphoric acid is polyphosphoric acid.

7. The method as set forth in claim 1 being particularly characterized in that a solid inert cushioning media is added to said aqueous solution and immersed metal article.

* * * * *